United States Patent [19]
Infeld et al.

[11] Patent Number: 5,393,765
[45] Date of Patent: Feb. 28, 1995

[54] PHARMACEUTICAL COMPOSITIONS WITH CONSTANT EROSION VOLUME FOR ZERO ORDER CONTROLLED RELEASE

[75] Inventors: Martin H. Infeld, Upper Montclair; A. Waseem Malick, Edison; Navnit H. Shah, Clifton; Wantanee Phuapradit, Kearny, all of N.J.

[73] Assignee: Hoffmann-La Roche Inc., Nutley, N.J.

[21] Appl. No.: 166,123

[22] Filed: Dec. 13, 1993

[51] Int. Cl.$^6$ .................. A61K 31/425; A61K 47/00; A61K 9/20
[52] U.S. Cl. .................................. 514/365; 424/464; 514/781
[58] Field of Search .................. 514/410, 365, 781; 424/19, 22, 177, 178, 180, 183, 201, 241, 243, 248, 258, 272, 285, 298, 310, 330, 362, 473, 464

[56] References Cited

U.S. PATENT DOCUMENTS

| | | |
|---|---|---|
| 3,870,790 | 3/1975 | Lowey et al. . |
| 4,226,849 | 10/1980 | Schor . |
| 4,259,314 | 3/1981 | Lowey . |
| 4,389,393 | 6/1983 | Schor et al. ............................ 424/19 |
| 4,540,566 | 9/1985 | Davis et al. ............................ 424/22 |
| 4,556,678 | 12/1985 | Hsiao .................................. 514/652 |
| 5,034,228 | 7/1991 | Meybeck et al. . |
| 5,126,145 | 6/1992 | Evenstad et al. .................... 424/465 |
| 5,213,808 | 5/1993 | Bar-Shalom et al. ................ 424/473 |
| 5,284,662 | 8/1994 | Kopaikai et al. ..................... 424/473 |

FOREIGN PATENT DOCUMENTS 0111144  6/1994  European Pat. Off. .

OTHER PUBLICATIONS

Theeuwes, Journal of Pharm. Sci. vol 64, No. 12, Elementary Osmotic Pump (1975).

Higuchi, Journal of Pharm. Sci. vol 52, No. 12, Mechanism of Sustained-Action Medication (1963).

Kallstrand, et al, Journal of Pharm. Sci. vol 72, No. 7, Membrane-Coated Tablets: A System for the Controlled Release of Drugs (1983).

*Primary Examiner*—Raymond J. Henley, III
*Assistant Examiner*—Keith MacMillan
*Attorney, Agent, or Firm*—George M. Gould; William H. Epstein; Catherine A. Picut

[57] ABSTRACT

An erodible pharmaceutical composition providing a unique zero order controlled release profile is herein described. The erodible composition contains a therapeutically active substance having a solubility not greater than 80 mg/mL, a hydroxypropyl methylcellulose derivative and erosion modifiers depending on drug solubility and drug loading, such as lactose and polyoxyalkylene derivatives of propylene glycol, as well as other inert materials such as binders and lubricants. The hydroxypropyl methylcellulose derivative is most preferably a hydroxy-propylmethyl having a methoxy content of about 19–30% and hydroxypropyl content of 7–12%, a methoxy degree of substitution from 1.1 to 2.0, a molecular weight of approximately 20,000 to 26,000 daltons and a viscosity of a 2% w/w polymer solution at 25° C. ranging from 50 to 100 cps. The composition erodes with a constant erosion volume for a desired time period. When ingested, the matrix forms two layers, an outer layer of hydrated matrix which is eroding and an inner core of unchanged matrix. The composition provides a zero order release profile in part because the diffusion rate of the drug from the matrix is either negligible or is comparable to the erosion rate of the matrix and the drug concentration in the hydrated layer remains constant.

11 Claims, 15 Drawing Sheets

PHARMACEUTICAL COMPOSITIONS WITH CONSTANT EROSION VOLUME FOR ZERO ORDER CONTROLLED RELEASE

BACKGROUND OF THE INVENTION

Controlled release dosage forms have received a great deal of attention for their use as drug delivery systems. These systems are capable of delivering a drug at a predetermined rate such that drug concentrations can be maintained at therapeutically effective levels over an extended period, with the potential for minimizing side effects.

Various approaches exist for the preparation of controlled release dosage forms. One commonly known technique is to form a matrix by entrapping the drug in excipients (i.e., cellulose ether derivatives). Diffusion and/or erosion operate to release the active substance, depending on the properties of the drug and the polymer incorporated in the formulation. This approach generally results in non-zero order release kinetics, T. Higuchi, J. Pharm. Sci., 52:1145 (1965). The amount of drug available at the absorption site therefore decreases with time, which is the major drawback of these dosage forms. In zero order release, the amount of drug release remains constant with respect to time. Prior methods for preparing zero order controlled release dosage forms include those operating by a rate-controlling membrane, G. Kallstrant, B. Ekman, J. Pharm. Sci., 72:772 (1983), and by osmotic pumps, F. Theeuwes, J. Pharm. Sci., 64:1987 (1975) and T. Higuchi, U.S. Pat. No. 4,439,196 (1984).

Dosage forms for controlled release applications containing cellulose ether derivatives are known. However, none of these prior formulations provides a zero order release form as described and claimed in this application.

U.S. Pat. No. 4,389,393 claims controlled release dosage forms made from a carrier base material comprising one or more hydroxypropyl methylcellulose (HPMC) or a mixture of one or more HPMC and up to 30% other cellulose ethers, where the carrier base comprises 25.8% or less of the total tablet weight.

U.S. Pat. No. 4,540,566 discloses the technology utilizing anionic surfactants to prolong drug release from a dosage form containing a low viscosity grade of HPMC.

U.S. Pat. No. 4,556,678 claims a controlled release propranolol formulation that utilizes HPMC and hydroxypropyl cellulose (HPC).

European Patent 109,320 relates to a theophylline composition that contains 18-35% HPMC, 7.5-22.5% of another hydrophilic binder and 0.5-1% of an internal hydrophobic lubricant.

European Patent 111,144 discloses a hydrophilic matrix tablet having one or more sustained release layers with differing drug concentrations using HPMC. The patent describes a hydrophilic matrix system using a gradient layer to achieve a zero order controlled release, this system applicable only for water soluble drugs.

SUMMARY OF THE INVENTION

An erodible pharmaceutical composition providing a unique zero order controlled release profile is herein described. The erodible composition contains a therapeutically active substance having a solubility not greater than 80 mg/mL, a hydroxypropyl methylcellulose derivative and erosion modifiers depending on drug solubility and drug loading, such as lactose and polyoxyalkylene derivatives of propylene glycol as well as other inert materials such as binders and lubricants. The hydroxypropyl methylcellulose derivative is most preferably a hydroxy-propylmethyl having a methoxy content of about 19-30% and hydroxypropyl content of 7-12%, a methoxy degree of substitution from 1.1 to 2.0, a molecular weight of approximately 20,000 to 26,000 daltons and viscosity of a 2% w/w polymer solution at 25° C. ranging from 50 to 100 cps. The composition erodes with a constant erosion volume for a desired time period. When ingested, the matrix forms two layers, an outer layer of hydrated matrix which is eroding and an inner core of unchanged matrix. The composition provides a zero order release profile, in part, because the diffusion rate of the drug from the matrix is either negligible or is comparable to the erosion rate of the matrix and the drug concentration in the hydrated layer remains constant.

DETAILED DESCRIPTION OF THE INVENTION

The present invention provides a means of achieving a zero order controlled release of a therapeutically active substance from an erodible pharmaceutical composition. Zero order release means that the rate of active substance released per time remains essentially constant throughout the lifespan of the composition. For example, a composition which releases 10% of the active ingredient per hour would release approximately 100% of the active substance in 10 hours.

The erodible pharmaceutical composition of this invention contains a drug or therapeutically active substance having a solubility not greater than 80 mg/mL, a low viscosity hydroxypropyl methylcellulose derivative and erosion modifiers, as needed, depending on drug solubility and drug loading. The composition delivers a drug at a constant rate for a period of time without prematurely breaking-up.

Figure 1:
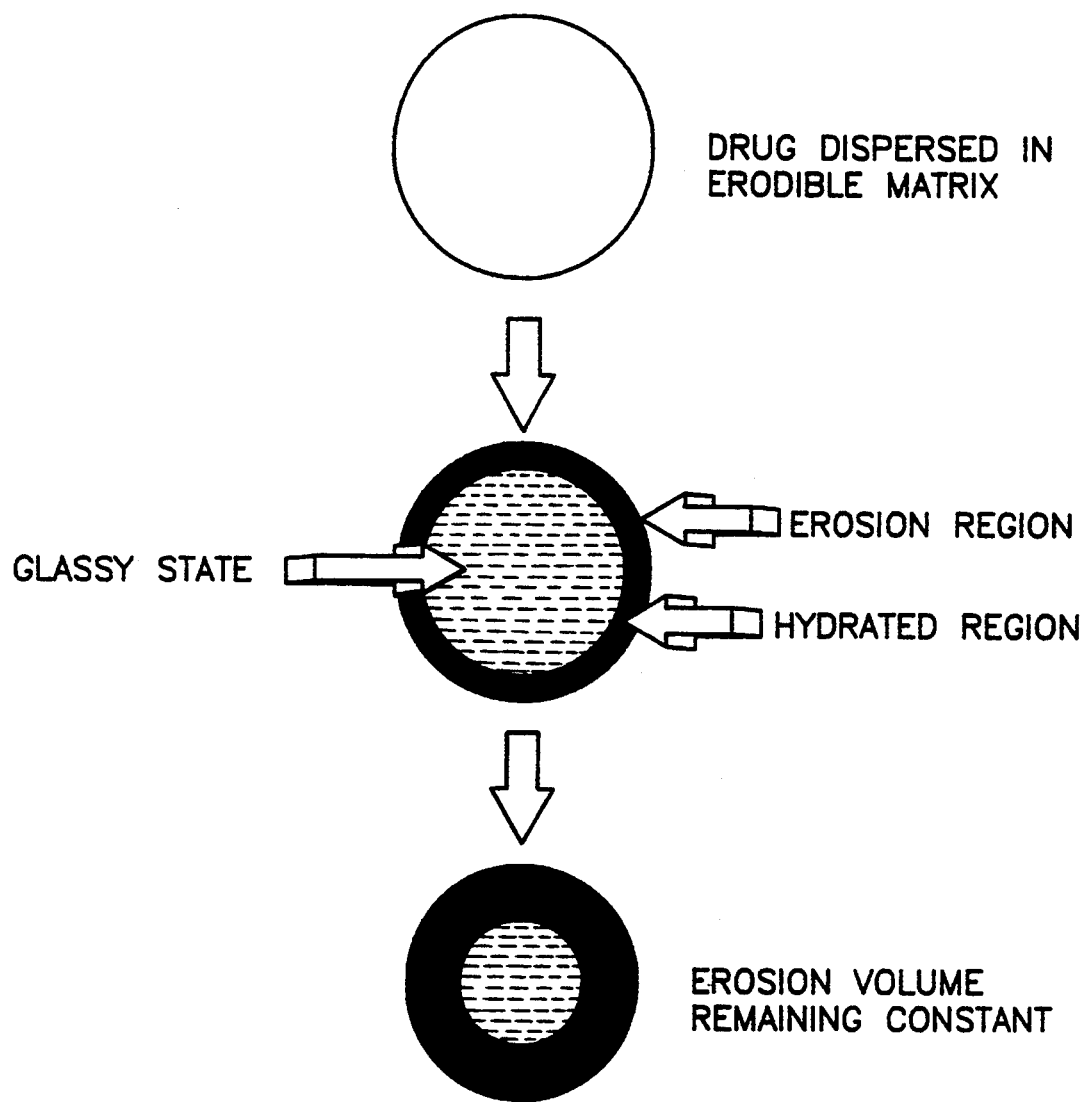
FIG. 1 is a schematic depiction of the dosage form of the pharmaceutical composition of the invention.

A schematic describing the release mechanism of the delivery system is depicted in FIG. 1. FIG. 1 depicts the matrix having an outer hydrated layer which erodes and an inner core which is unchanged. In the compositions of the present invention, the diffusion rate of the drug from the matrix is negligible or is comparable to the erosion rate of the matrix and the drug concentration in the hydrated layer remains constant. The drug release is controlled by a constant erosion volume of the matrix. The amount of drug released at time t ($M_t$) is described by the following equation:

$$M_t = V_t C \quad \text{(Eq. 1)}$$

$$dV_t/dt = k_o \quad \text{(Eq. 2)}$$

where $V_t$ is the volume of the hydrated layer eroded at time t; C is the concentration of drug in the hydrated layer; and $dV_t/dt$ is the erosion rate ($k_o$) which is constant.

The drug release rate, $dM_t/dt$, is zero order when the drug concentration in the hydrated layer, C, remains constant. The dissolution or erosion of the matrix itself, following hydration of the HPMC, results in the release of the active ingredient dispersed in the matrix.

In accordance with the present invention, formulations for the preparation of the erodible compositions for oral administration having zero order release are prepared as described below. The active ingredient was mixed with a cellulose ether derivative, such as Methocel® K100 LV, and an erosion modifier, such as lactose or a nonionic surfactant, such as polyoxyalkylene derivatives of propylene glycol (sold under the tradename Pluronic F-68), as a direct blend or wet granulated with appropriate binders such as polyvinylpyrrolidone or hydroxypropyl cellulose. Polyvinylpyrrolidone is available under the tradename Povidone. Klucel LF is a commercially available hydroxypropyl cellulose. The wet granulation was dried at 50° C. and screened through a #30 mesh screen. A lubricant such as magnesium stearate was blended with the dried granulation. Using a suitable tablet press, the granulation was compressed into a tablet having the specified weight. The active ingredient is present in the composition in an amount ranging from 5% to 60% w/w of the composition.

The erodible composition is formed by the combination of a therapeutically active substance, a cellulose ether derivative and when desired, an erosion modifier such as lactose or Pluronic F-68. The cellulose ether derivative is present in the matrix in an amount ranging from 5% to 50% w/w. A preferred composition contains the cellulose ether derivative in an amount ranging from 10% to 25% w/w.

Examples of the cellulose ether derivatives that can be suitably employed in accordance with this invention include hydroxypropyl methylcellulose or hydroxypropyl cellulose or their mixtures. A most preferred erodible matrix is hydroxypropyl methylcellulose having a methoxy content of about 19–30% and hydroxypropyl content of 7–12%, a methoxy degree of substitution from 1.1 to 2.0 and molecular weight of approximately 20,000 to 26,000 daltons. A 2% w/w polymer solution exhibits a gel point of 62°–90° C. and a viscosity at 25° C. ranging from 50 to 100 cps.

Solubility of the exemplary drugs in water at 25° C. is as follows:

| Drug | Solubility |
|---|---|
| (E)-4-[[3-[2-(4-Cyclobutyl-2-thiazolyl)ethenyl]phenyl]amino]-2,2-diethyl-4-oxobutanoic acid | <2 µg/mL |
| (+)-cis-3-(Acetyloxy)-2,3-dihydro-2-(4-methoxyphenyl)-5-[2-(dimethylamino)ethyl]naphtho[1,2-b]-1,4-thiazepin-4(5H)-one | 80 mg/mL |
| Cibenzoline Succinate | 26.30 mg/mL |
| 4-(2,2-Diphenylethenyl)-1-[1-oxo-9-(3-pyridinyl)nonyl]piperidine | 0.182 µg/mL |
| 7-Chloro-N-methyl-5-(1H-pyrrol-2-yl)-3H-1,4-benzodiazepin-2-amine | 1.5 µg/mL |
| 5-[3-[4-(2-Chlorophenyl)-9-methyl-6H-thieno[3,2-f][1,2,4]triazolo[4,3-a][1,4]diazepin-2-yl]-2-propynyl]phenanthrydin-6(5H)-one | 0.01 µg/mL |

The zero-order release drug delivery system of this invention is applicable to drugs such as Nifedipine, (E)-4-[[3-[2-(4-Cyclobutyl-2-thiazolyl)ethenyl]phenyl]amino]-2,2-diethyl-4-oxobutanoic acid, (+)-cis-3-(Acetyloxy)-2,3-dihydro-2-(4-methoxyphenyl)-5-[2-dimethylamino)ethyl]naphtho[1,2-b]-1,4-thiazepin-4(5H)-one, Cibenzoline Succinate and Diltiazem.

The evaluation of drug release from the erodible matrix was performed using the USP dissolution test procedure with either the Basket or Paddle Method at the speed as specified. The Basket and Paddle methods are described on page 1578 of U.S. Pharmacopeia (USP) XXII & National Formulary (NF) XVII (The United States Pharmacopeial Convention, Inc., Rockville, Md., 1990). Briefly, in both methods, one tablet is placed in the appropriate apparatus described below containing the specified amount of dissolution medium and the stirring element is started. The amount of drug in solution is determined by the UV spectrophotometric method as is known in the art. The assembly used in the Basket Method consists of the following: a covered vessel made of glass with nominal capacity 1000 mL; a motor; a metallic drive shaft; and a cylindrical basket. The vessel containing 900 mL of the specified dissolution medium (i.e., water, 1% nonionic surfactant Emulphor ON-870 in phosphate buffer, pH 7.5 or 3% sodium lauryl sulfate, pH 9.0) is partially immersed in a suitable water bath and equilibrated at 37°±0.5° C. A fitted cover may be used to retard evaporation. The shaft is positioned so that its axis is not more than 2 mm at any point from the vertical axis of the vessel and rotates smoothly and without significant wobble. A speed-regulating device is used that allows the shaft rotation speed to be selected and maintained at the specified rate. The recommended basket speed is 100 rpm. The distance between the inside bottom of the vessel and the basket is maintained at 25±2 mm during the test.

The assembly used in the Paddle method is the same as the apparatus used in the Basket Method, except that a paddle formed from a blade and a shaft is used as the stirring element. The shaft is positioned so that its axis is not more than 2 mm at any point from the vertical axis of the vessel, and rotates smoothly and without significant wobble. The recommended speed of the paddle is 50 rpm. The distance of 25±2 mm between the blade and inside bottom of the vessel is maintained during the test. The dissolution medium was used as specified (i.e., 900 mL of simulated gastric fluid or 1% nonionic surfactant Emulphor ON-870 in phosphate buffer, pH 7.5 at 37° C.). The drug analysis was determined by UV spectrophotometry.

The erosion profile of a tablet is determined by using USP Apparatus 1 (Basket Method). The procedure is similar to the method described above for evaluating drug release. The tablet is placed in the USP basket and immersed in 900 mL of purified water using a speed of 100 rpm. At a specified time interval, the basket with the remaining tablet is removed from the medium and the tablet is dried in an oven at 50° C. for at least 18 hours and/or until a constant weight is obtained. The percent erosion is calculated based on the weight loss of the tablet.

As shown in FIGS. 2-7 and 9-15, the pharmaceutical compositions of the invention produce zero order release profiles in the given dissolution medium. The use of a highly soluble drug such as chlorpheniramine maleate in a pharmaceutical composition with the polymer of the present invention does not produce a zero-order release profile in the dissolution medium as is shown in FIG. 8 due to additional diffusion of the active substance.

Figure 4:
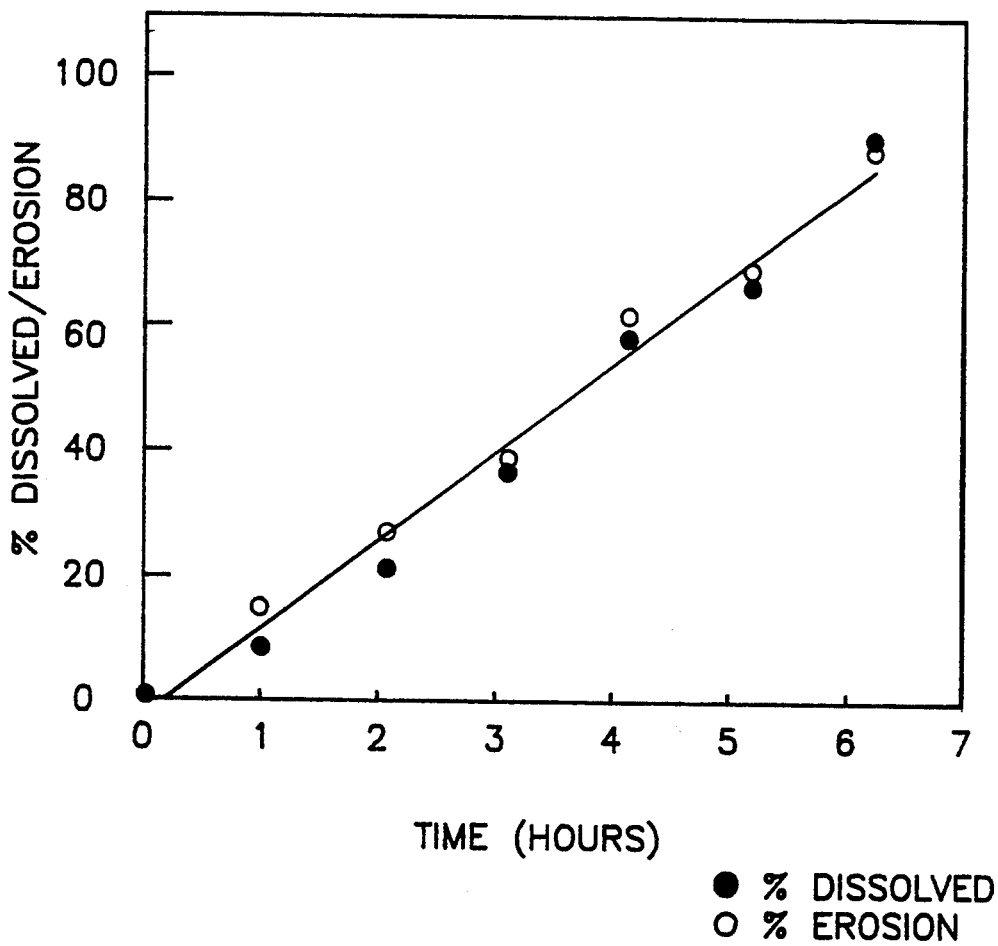
FIG. 4 shows the release and erosion profiles of the pharmaceutical composition of Example 1 in 900 mL of 1% Emulphor ON-870 in phosphate buffer (pH 7.5) at 37° C. using the Basket Method at a speed of 100 rpm.

FIG. 4 shows that the release rate of the therapeutically active agent from the pharmaceutical composition is closely correlated with the erosion rate of the composition.

The controlled release (CR) matrix composition of this invention is further illustrated by, but not limited to, the following examples.

EXAMPLE 1

| Ingredients | mg/tablet |
| --- | --- |
| (E)-4-[[3-[2-(4-Cyclobutyl-2-thiazolyl)ethenyl]phenyl]amino]-2,2-diethyl-4-oxobutanoic acid) | |
| Pluronic F68 | 100.0 |
| Methocel K100LV | 135.0 |
| Hydrous Lactose | 135.0 |
| Povidone K30 | 28.5 |
| Magnesium Stearate | 1.5 |

Figure 2:
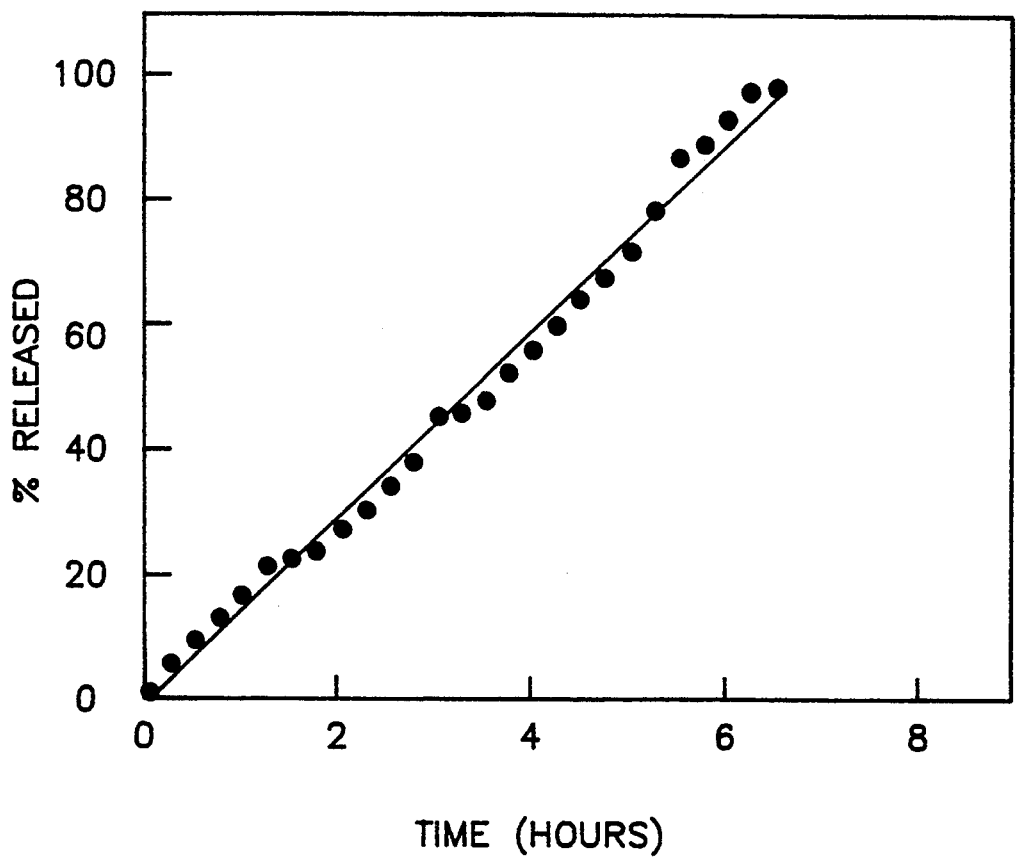
FIG. 2 shows the release profile of the pharmaceutical composition of Example 1 in 900 mL of 1% Emulphor ON-870 in phosphate buffer (pH 7.5) at 37° C. using the Basket Method at a speed of 100 rpm.
Figure 3:
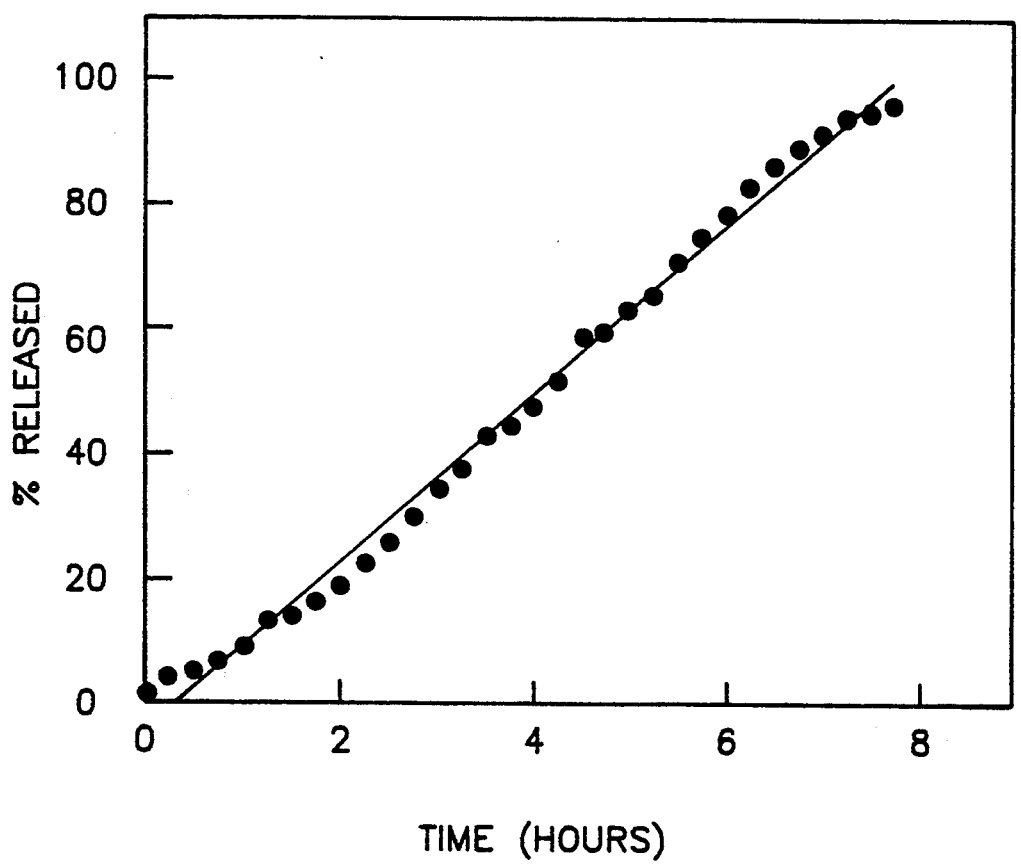
FIG. 3 shows the release profile of the pharmaceutical composition of Example 1 in 900 mL of 1% Emulphor ON-870 in phosphate buffer (pH 7.5) at 37° C. using the Paddle Method at a speed of 50 rpm.

The release profiles of 100 mg CR Tablets are shown in FIGS. 2 and 3. A comparison of the release and erosion profiles of (E)-4-[[3-[2-(4-Cyclobutyl-2-thiazolyl)ethenyl]phenyl]amino ]-2,2-diethyl-4-oxobutanoic acid) 100 mg CR Tablets is shown in FIG. 4.

EXAMPLE 2

| Ingredients | mg/tablet |
| --- | --- |
| (E)-4-[[3-[2-(4-Cyclobutyl-2-thiazolyl)ethenyl]phenyl]amino]-2,2-diethyl-4-oxobutanoic acid) | 100.0 |
| Povidone K30 | 20.0 |
| Methocel K100LV | 31.2 |
| Anhydrous Lactose | 46.8 |
| Magnesium Stearate | 2.0 |

Figure 5:
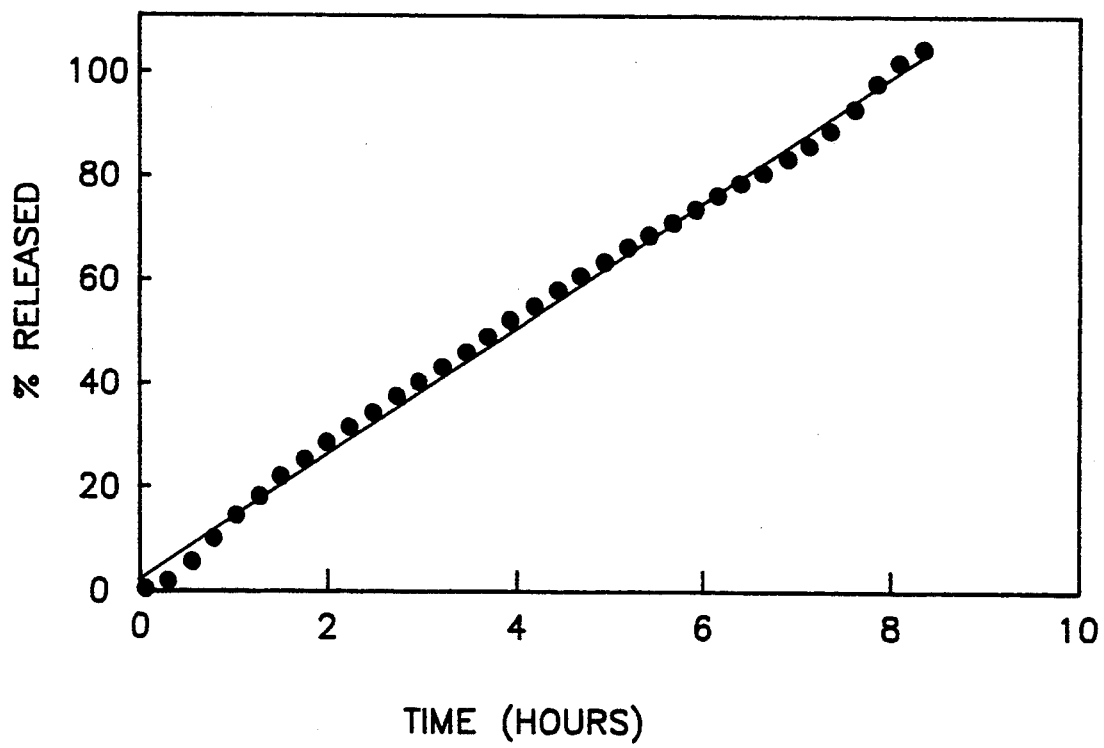
FIG. 5 shows the release profile of the pharmaceutical composition of Example 2 in 900 mL of 1% Emulphor ON-870 in phosphate buffer (pH 7.5) at 37° C. using the Paddle Method at a speed of 50 rpm.

The release profile of (E)-4-[[3-[2-(4-Cyclobutyl-2-thiazolyl)ethenyl]phenyl]amino]-2,2-diethyl-4-oxobutanoic acid) 100 mg CR Tablets is shown in FIG. 5.

EXAMPLE 3

| Ingredients | mg/tablet |
| --- | --- |
| (+)-cis-3-(Acetyloxy)-2,3-dihydro-2-(4-methoxyphenyl)-5-[2-(dimethylamino)ethyl]naphtho[1,2-b]-1,4-thiazepin-4(5H)-one | 54.0 |
| Anhydrous Lactose | 200.0 |
| Methocel K100LV | 125.0 |
| Povidone K30 | 20.0 |
| Magnesium Stearate | 3.0 |

Figure 6:
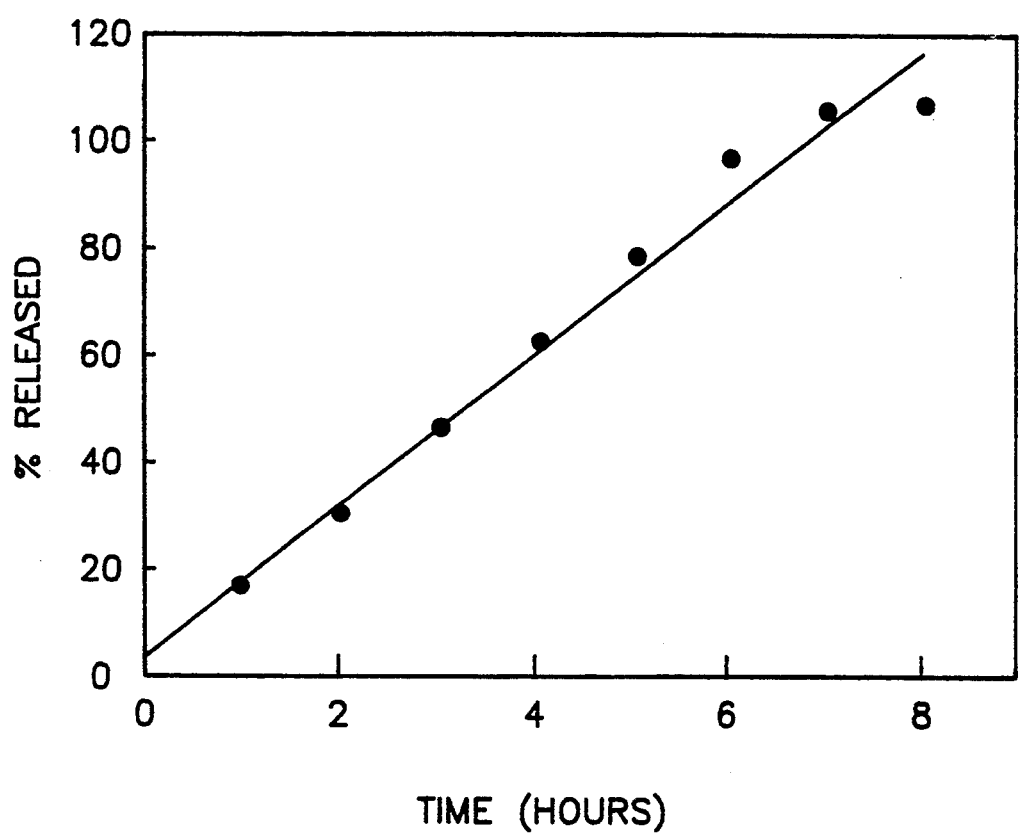
FIG. 6 shows the release profile of the pharmaceutical composition of Example 3 in 900 mL of simulated gastric fluid at 37° C. using the Paddle Method at a speed of 50 rpm.

The release profile of (+)-cis-3-(Acetyloxy)-2,3-dihydro-2-(4-methoxyphenyl) -5-[2-(dimethylamino)ethyl]naphtho[1,2-b]-1,4-thiazepin-4(5H)-one 54 mg CR Tablets is shown in FIG. 6.

EXAMPLE 4

| Ingredients | mg/tablet |
| --- | --- |
| Cibenzoline Succinate | 232.0 |
| Methocel K100LV | 200.0 |
| Povidone K30 | 50.0 |
| Stearic Acid | 5.0 |
| Syloid 244 | 5.0 |
| Magnesium Stearate | 10.0 |

Figure 7:
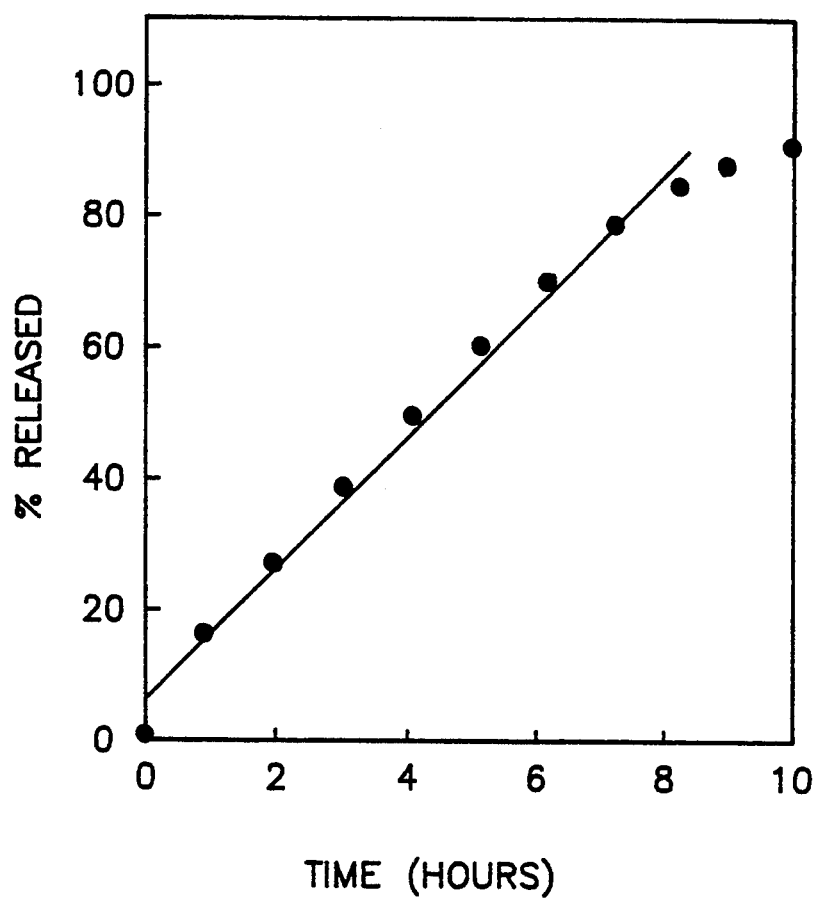
FIG. 7 shows the release profile of the pharmaceutical composition of Example 4 in 900 mL of water at 37° C. using the Basket Method at a speed of 100 rpm.
Figure 8:
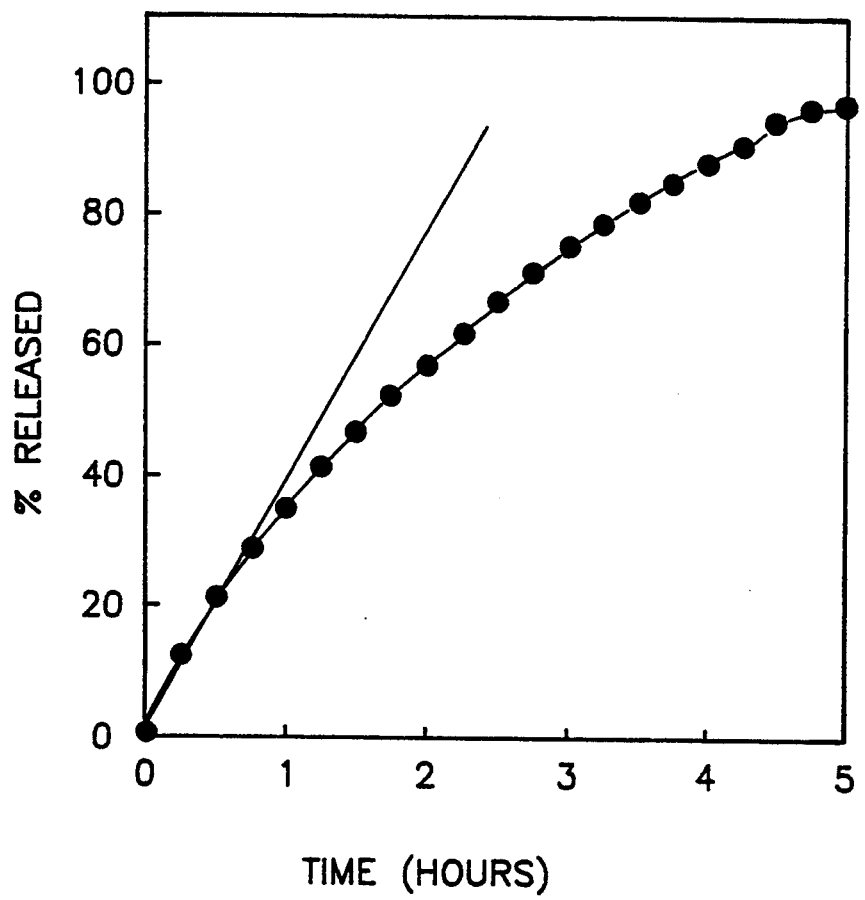
FIG. 8 shows the release profile of the pharmaceutical composition of Example 5 in 900 mL of water at 37° C. using the Basket Method at a speed of 100 rpm.

The release profile of Cibenzoline Succinate CR Tablets is shown in FIG. 7.

EXAMPLE 5

| Ingredients | mg/tablet |
| --- | --- |
| Chlorpheniramine | 54 |

-continued

| Ingredients | mg/tablet |
|---|---|
| Maleate | |
| Anhydrous Lactose | 200 |
| Methocel K100LV | 125 |
| Povidone K30 | 20 |
| Magnesium Stearate | 6 |

The release profile of the chlorpheniramine maleate tablet is shown in FIG. 8.

EXAMPLE 6

| Ingredients | mg/tablet |
|---|---|
| (E)-4-[[3-[2-(4-Cyclobutyl-2-thiazolyl)ethenyl]phenyl]amino]-2,2-diethyl-4-oxobutanoic acid) | 300.0 |
| Methocel K100LV | 52.9 |

Figure 9:
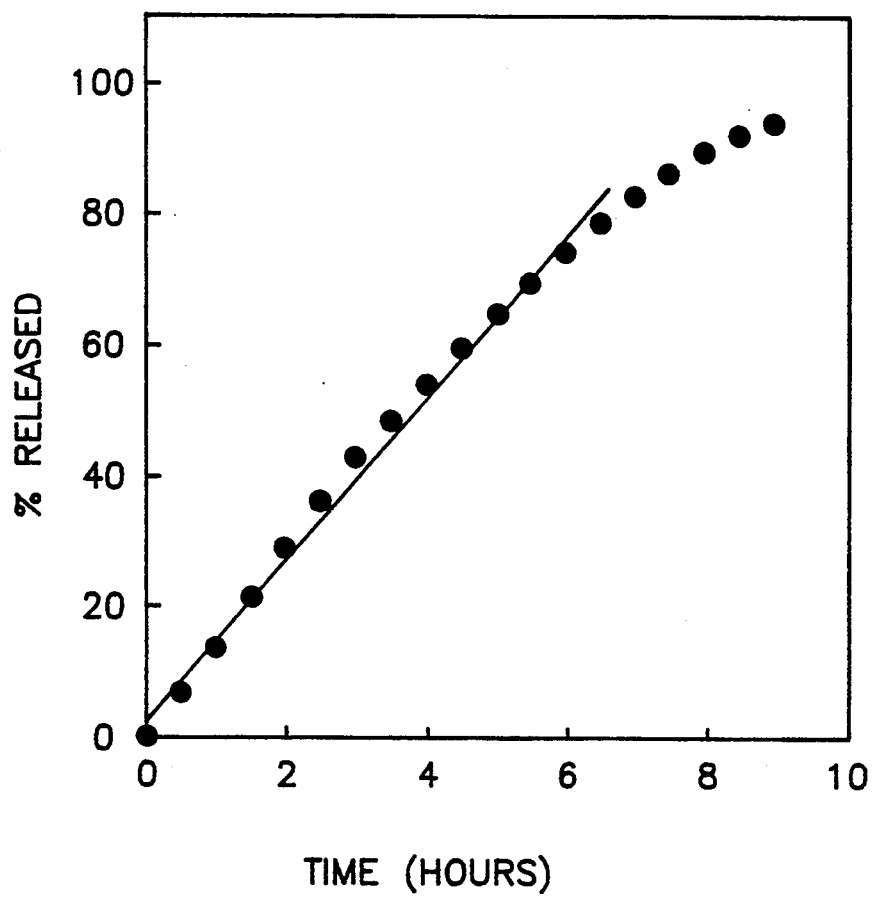
FIG. 9 shows the release profile of the pharmaceutical composition of Example 6 in 900 mL of water containing 3% sodium lauryl sulfate (pH 9.0) at 37° C. using the Basket Method at a speed of 100 rpm.

The release profile of the tablet is shown in FIG. 9.

EXAMPLE 7

| Ingredients | mg/tablet |
|---|---|
| (E)-4-[[3-[2-(4-Cyclobutyl-2-thiazolyl)ethenyl]phenyl]amino]-2,2-diethyl-4-oxobutanoic acid) | 300 |
| Klucel LF | 18 |
| Methocel K100LV | 60 |
| Anhydrous Lactose | 216 |
| Magnesium Stearate | 6 |

Figure 10:
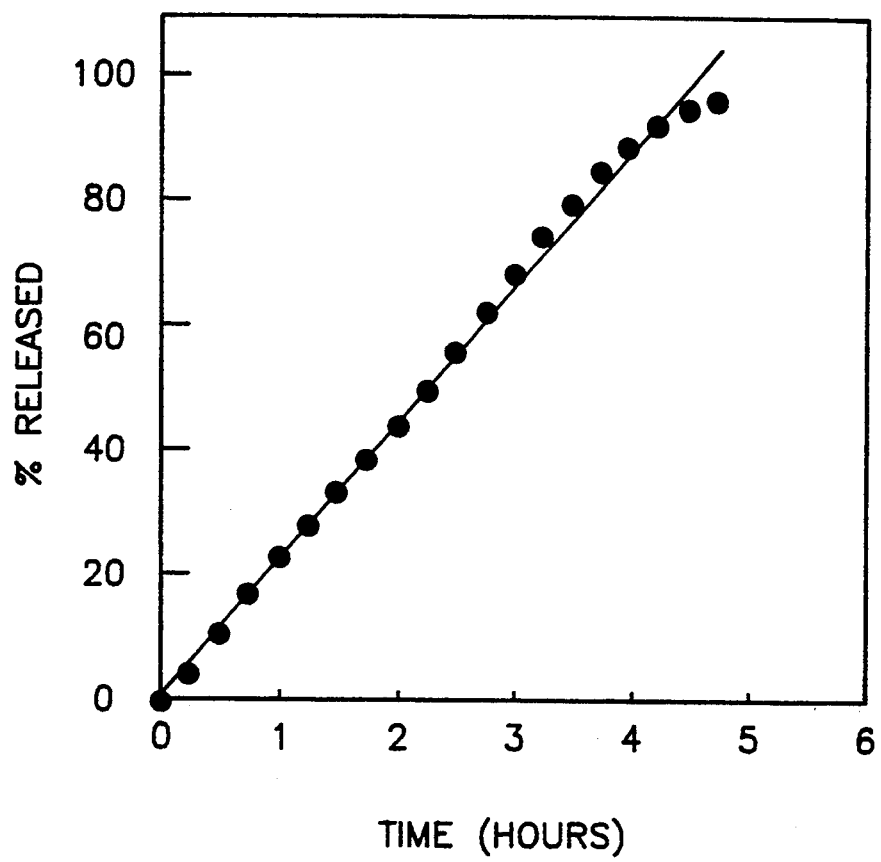
FIG. 10 shows the release profile of the pharmaceutical composition of Example 7 in 900 mL of water containing 3% sodium lauryl sulfate (pH 9.0) at 37° C. using the Basket Method at a speed of 100 rpm.

The release profile of the tablet is shown in FIG. 10.

EXAMPLE 8

| Ingredients | mg/tablet |
|---|---|
| (E)-4-[[3-[2-(4-Cyclobutyl-2-thiazolyl)ethenyl]phenyl]amino]-2,2-diethyl-4-oxobutanoic acid) | 300 |
| Klucel LF | 18 |
| Methocel K100LV | 30 |
| Anhydrous Lactose | 246 |
| Magnesium Stearate | 6 |

Figure 11:
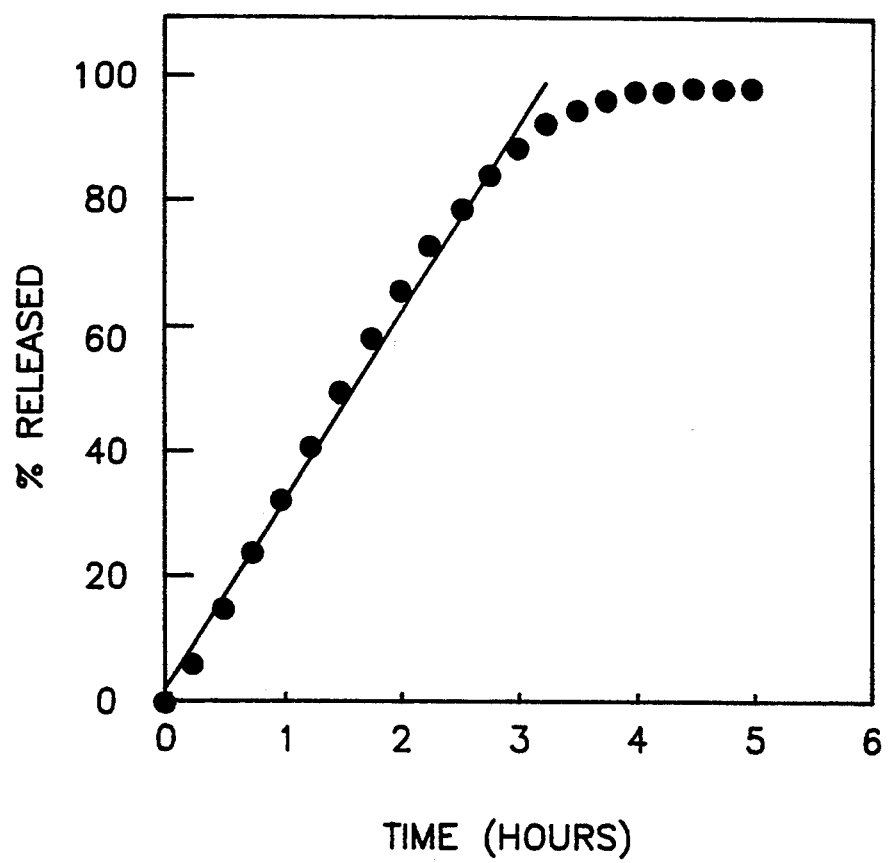
FIG. 11 shows the release profile of the pharmaceutical composition of Example 8 in 900 mL of water containing 3% sodium lauryl sulfate (pH 9.0) at 37° C. using the Basket Method at a speed of 100 rpm.

The release profile of the tablet is shown in FIG. 11.

EXAMPLE 9

| Ingredients | mg/tablet |
|---|---|
| (E)-4-[[3-[2-(4-Cyclobutyl-2-thiazolyl)ethenyl]phenyl]amino]-2,2-diethyl-4-oxobutanoic acid) | 300 |
| Methocel K100LV | 90 |
| Klucel LF | 18 |
| Lactose Anhydrous | 186 |
| Magnesium Stearate | 6 |

Figure 12:
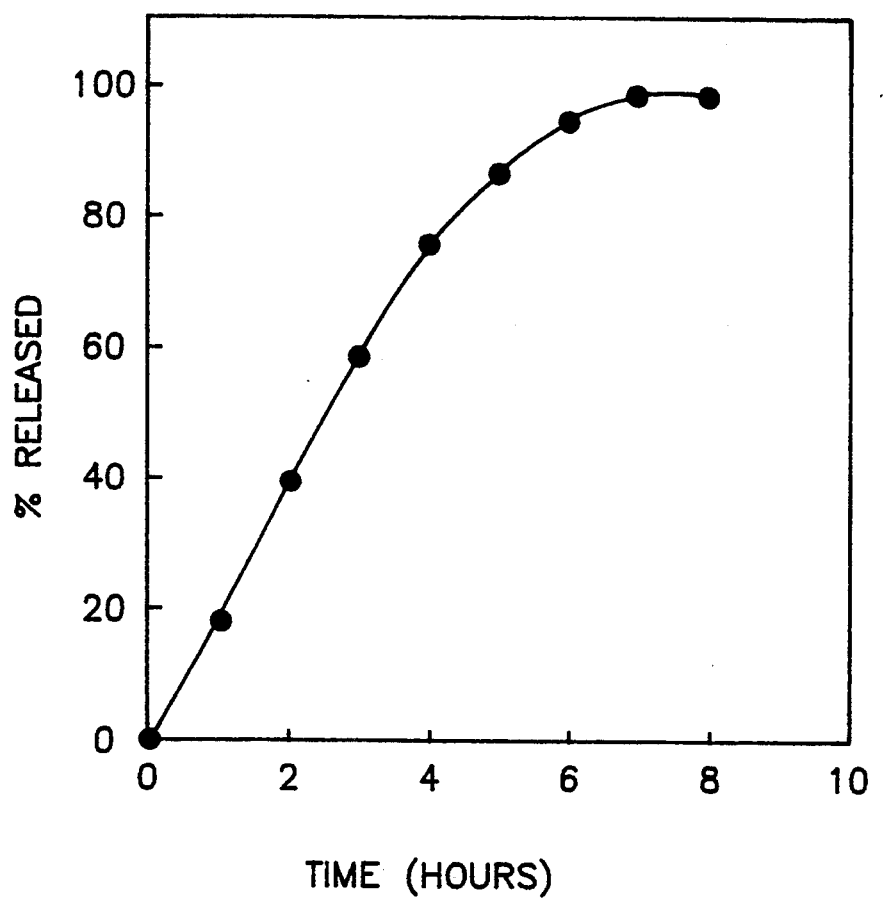
FIG. 12 shows the release profile of the pharmaceutical composition of Example 9 in 900 mL of water containing 3% sodium lauryl sulfate (pH 9.0) at 37° C. using the Basket Method at a speed of 100 rpm.

The release profile of the tablet is shown in FIG. 12.

EXAMPLE 10

| Ingredients | mg/tablet |
|---|---|
| 4-(2,2-Diphenylethenyl)-1-[1-oxo-9-(3-pyridinyl)nonyl]piperidine, micronized | 300 |
| Klucel LF | 18 |
| Anhydrous Lactose | 150 |
| Methocel K100LV | 126 |
| Magnesium Stearate | 6 |

Figure 13:
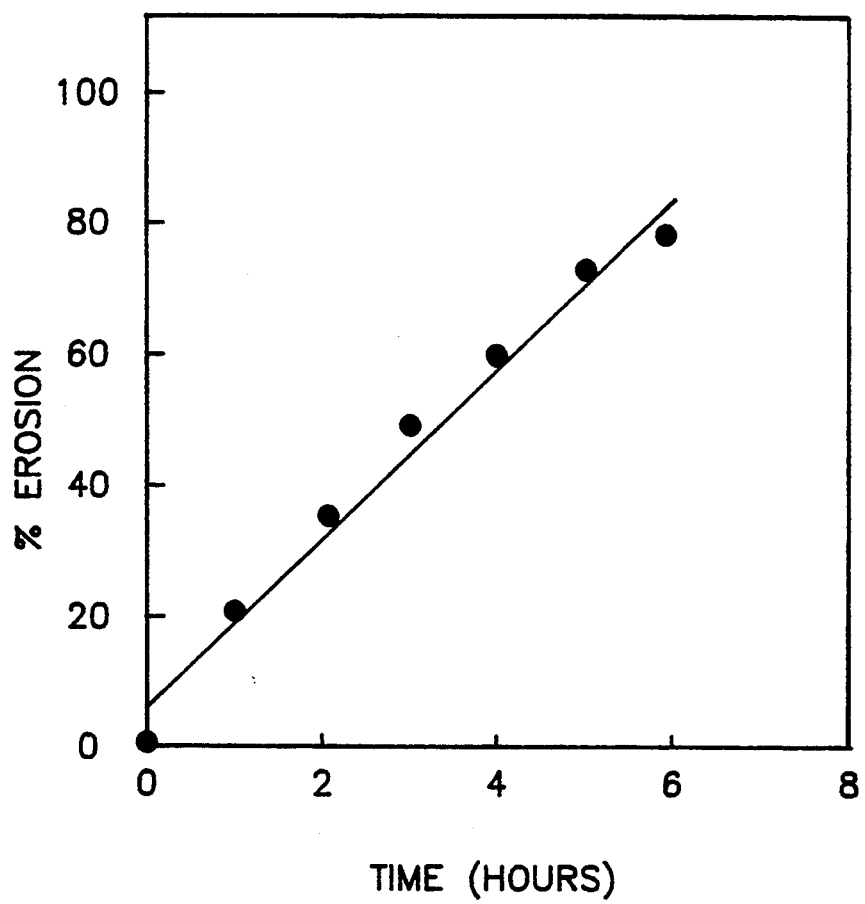
FIG. 13 shows the erosion profile of the composition of Example 10 in 900 mL of water containing 3% sodium lauryl sulfate (pH 9.0) at 37° C. using the Basket Method at a speed of 100 rpm.

The erosion profile of the tablet is shown in FIG. 13.

EXAMPLE 11

| Ingredients | mg/tablet |
|---|---|
| 7-Chloro-N-methyl-5-(1H-pyrrol-2-yl)-3H-1,4-benzodiazepin-2-amine, micropulverized | 300 |
| Klucel LF | 18 |
| Anhydrous Lactose | 150 |
| Methocel K100LV | 126 |
| Magnesium Stearate | 6 |

Figure 14:
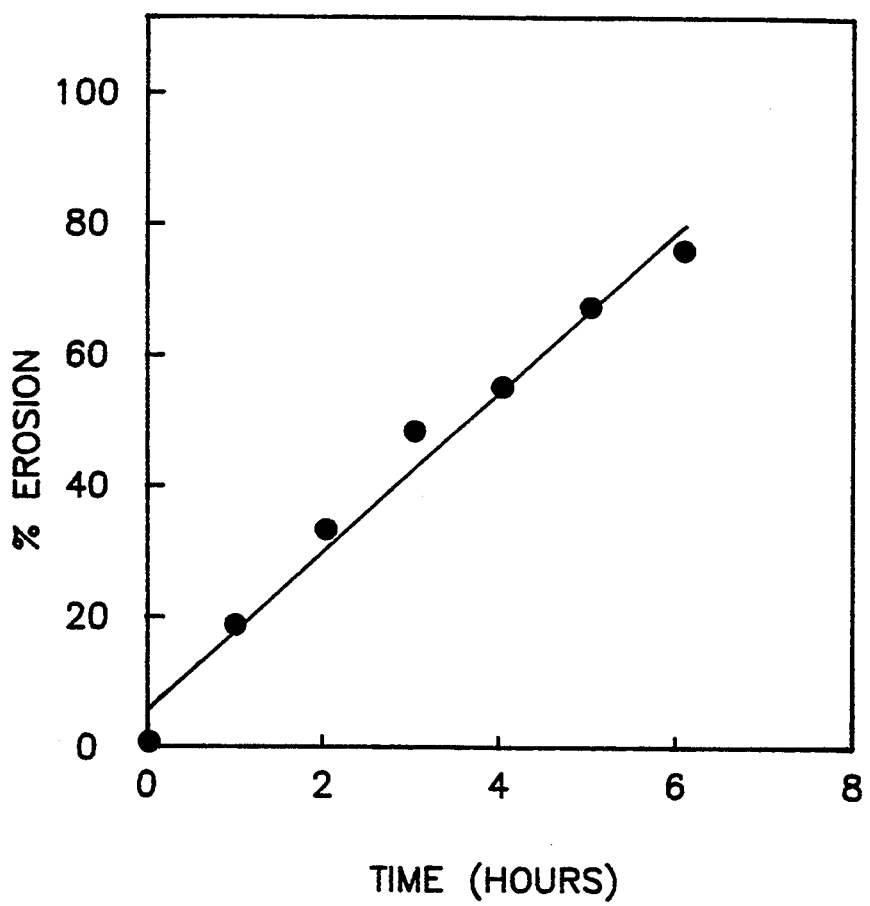
FIG. 14 shows the erosion profile of the composition of Example 11 in 900 mL of water at 37° C. using the Basket Method at a speed of 100 rpm.

The erosion profile of the tablet is shown in FIG. 14.

EXAMPLE 12

| Ingredients | mg/tablet |
|---|---|
| 5-[3-[4-(2-Chlorophenyl)-9-methyl-6H-thieno[3,2-f][1,2,4]triazolo[4,3-a][1,4]diazepin-2-yl]-2-propynyl]phenanthrydin-6(5H)-one, micronized | 75 |
| Klucel LF | 9 |
| Anhydrous Lactose | 113 |
| Methocel K100LV | 100 |
| Magnesium Stearate | 3 |

Figure 15:
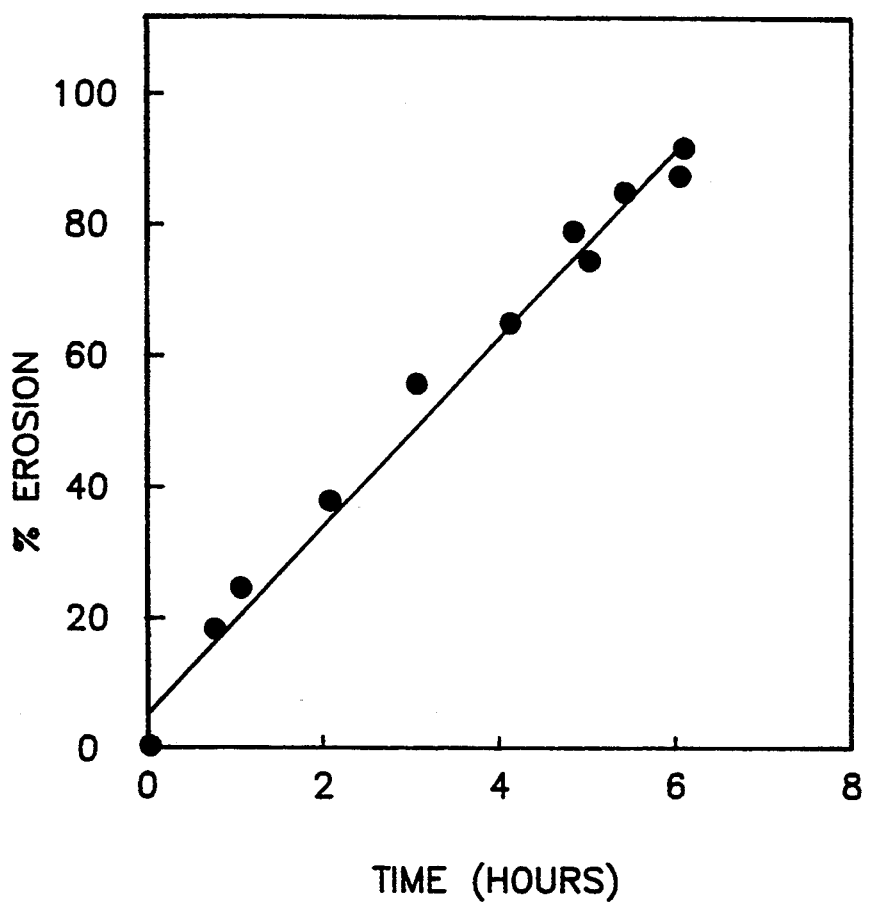
FIG. 15 shows the erosion profile of the composition of Example 12 in 900 mL of water at 37° C. using the Basket Method at a speed of 100 rpm.

The erosion profile of the tablet is shown in FIG. 15.

We claim:

1. An erodible pharmaceutical composition, shaped and compressed to a solid unit dosage form, which provides a zero order controlled release of a therapeutically active substance, the erodible composition comprising between about 5% to about 60% w/w of a therapeutically active substance which has a solubility of less than 80 mg/mL and at least about 5% up to about 50% w/w of hydroxypropyl methylcellulose having a viscosity from about 50 to about 100 centipoises and the remainder of the erodible composition consisting of inert carriers.

2. An erodible pharmaceutical composition of claim 1 wherein the hydroxypropyl methylcellulose has a methoxy content of about 19–30%, a hydroxypropyl content of 7–12%, a methoxy degree of substitution from 1.1 to 2.0, a molecular weight of approximately 20,000 to 26,000 daltons and wherein a 2% w/w solution of the polymer has a viscosity at 25° C. in the range of 50 to 100 cps.

3. An erodible pharmaceutical composition of claim 1 wherein the therapeutically active substance is (E)-4-[[3-[2-(4-Cyclobutyl-2-thiazolyl)ethenyl]phenyl]amino]-2,2-diethyl-4-oxobutanoic acid.

4. An erodible pharmaceutical composition of claim 1 wherein the hydroxypropyl methylcellulose is present in an amount between 10% to 25% w/w of the matrix.

5. An erodible pharmaceutical composition, shaped and compressed to a solid unit dosage form, which provides a zero order controlled release of a therapeutically active substance, the erodible composition comprising between about 5% to 60% w/w of a therapeutically active substance which has a solubility of less than 80 mg/mL, at least about 5% up to about 50% w/w of a low viscosity hydroxypropyl methylcellulose, at least about 10% up to about 60% w/w of an erosion modifier and the remainder of the erodible composition consisting of inert carriers.

6. An erodible pharmaceutical composition of claim 5 wherein the erosion modifier is lactose.

7. An erodible pharmaceutical composition of claim 5 wherein the erosion modifier is a non-ionic surfactant.

8. An erodible pharmaceutical composition of claim 5 wherein the therapeutically active substance is (E)-4-[[3-[2-(4-Cyclobutyl-2-thiazolyl)ethenyl]phenyl]amino]-2,2-diethyl-4-oxobutanoic acid.

9. An erodible pharmaceutical composition of claim 8 wherein (E)-4-[[3-[2-(4-Cyclobutyl-2-thiazolyl)ethenyl]phenyl]amino]-2,2-diethyl-4-oxobutanoic acid is present in the amount of 50% w/w, the low viscosity hydroxypropyl methylcellulose is present in the amount of 10% w/w and the erosion modifier is lactose and is present in the amount of 40% w/w.

10. An erodible pharmaceutical composition of claim 8 wherein (E)-4-[[3-[2-(4-Cyclobutyl-2-thiazolyl)ethenyl]phenyl]amino]-2,2-diethyl-4-oxobutanoic acid is present in the amount of 50% w/w, the low viscosity hydroxypropyl methylcellulose is present in the amount of 15% w/w and the erosion modifier is lactose and is present in the amount of 35% w/w.

11. An erodible pharmaceutical composition of claim 8 wherein (E)-4-[[3-[2-(4-Cyclobutyl-2-thiazolyl)ethenyl]phenyl]amino]-2,2-diethyl-4-oxobutanoic acid is present in the amount of 50% w/w, the low viscosity hydroxypropyl methylcellulose is present in the amount of 25% w/w and the erosion modifier is lactose and is present in the amount of 25% w/w.

* * * * *